(12) United States Patent
Hutten et al.

(10) Patent No.: US 6,934,577 B2
(45) Date of Patent: Aug. 23, 2005

(54) RISK MONITORING

(75) Inventors: Helmut Hutten, Graz (AT); Martin Hribernigg, Graz-Goesting (AT); Günter Rauchegger, Graz-Goesting (AT)

(73) Assignee: Biotronik Mess- und Therapiegeraete GmbH & Co. Ingeieurbuero Berlin, Berlin (DE)

( * ) Notice: Subject to any disclaimer, the term of this patent is extended or adjusted under 35 U.S.C. 154(b) by 643 days.

(21) Appl. No.: 09/961,874

(22) Filed: Sep. 24, 2001

(65) Prior Publication Data

US 2002/0095094 A1 Jul. 18, 2002

(30) Foreign Application Priority Data

Sep. 26, 2000 (DE) .......................................... 100 48 649

(51) Int. Cl.⁷ ................................................. A61B 5/04
(52) U.S. Cl. ...................................................... 600/515
(58) Field of Search ........................................... 600/515

(56) References Cited

U.S. PATENT DOCUMENTS

| | | | |
|---|---|---|---|
| 4,499,904 A | 2/1985 | Sidorenko | |
| 5,113,869 A | 5/1992 | Nappholz | |
| 5,437,285 A | 8/1995 | Verrier | |
| 5,471,991 A | 12/1995 | Shinnar | |
| 6,120,441 A | 9/2000 | Griebel | |
| 6,496,722 B1 | 12/2002 | Schmidt | |

FOREIGN PATENT DOCUMENTS

| | | |
|---|---|---|
| DE | 211 922 | 7/1984 |
| DE | 2 190 505 A | 11/1987 |
| DE | 44 05 827 A1 | 6/1995 |
| DE | 44 05 827 A | 6/1995 |
| DE | 195 17 138 A1 | 11/1996 |
| DE | 195 38 473 A1 | 4/1997 |
| DE | 197 49 393 A1 | 5/1999 |
| WO | WO 99/23944 A1 | 5/1999 |

OTHER PUBLICATIONS

Weisner, Steven J. et al, "A Compact, Microprocessor–Based ECG ST–segment Analyzer for the Operating Room," Trans.Biomed.Engrgr, IEEE (US), vol. 29 (No. 9), p. 642–9, (Sep. 2, 1982).

Breidhardt, Von G. et al, "Heutiger Stand und Probleme der Computeranalyse von Extrasystolen," Med. Technik, vol. 93 (No. 5), p. 114–9, ( May 2, 1973).

Universitaets–Rechenzentrum Trier, "Logistische Regressionasanalyse," Universitaets–Rechenzentrum Trier (Trier, Germany), p. 4–22, ( Dec. 16, 1999).

Primary Examiner—Mark Bockelman
(74) Attorney, Agent, or Firm—Hahn Loeser & Parks LLP

(57) ABSTRACT

A risk assessment device, in particular for the risk of a severe heart functional disorder such as sudden death due to heart disease, comprising an input unit which is adapted to record or read in an electrocardiographic input signal and to output a corresponding output signal comprising a plurality of cardiac cycles and corresponding intervals, and a detection unit which is connected to the input unit and which is adapted to detect events of predetermined nature in the output signal, wherein there are provided a summing unit which is connected to the detection unit and the input unit and is adapted to add up the length of predetermined intervals connected to a detected event within the input signal and to output a corresponding sum parameter, and an evaluation unit which is adapted to evaluate the sum parameter under predetermined conditions and to output a risk parameter which is dependent on the evaluation.

36 Claims, 1 Drawing Sheet

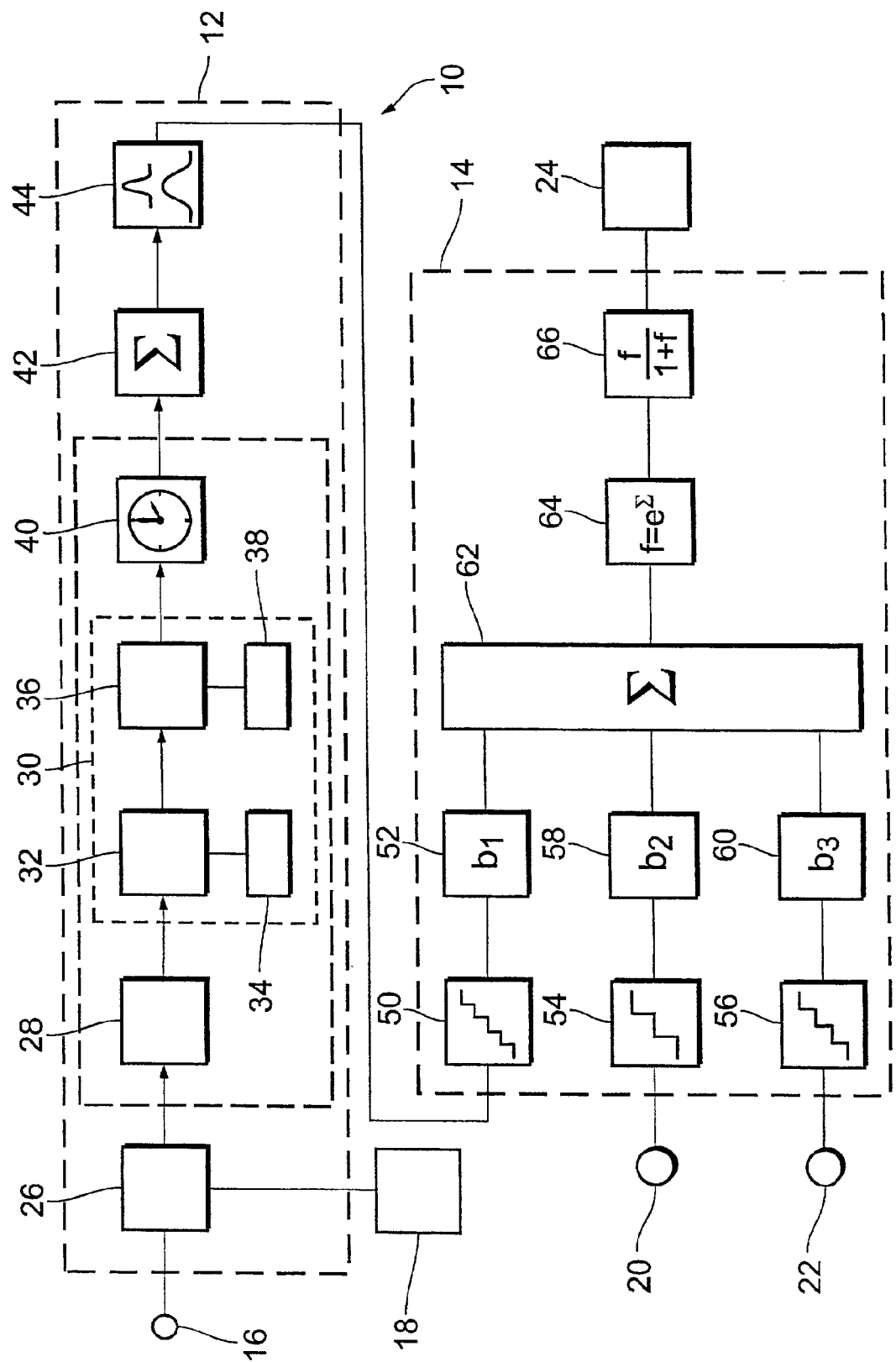

RISK MONITORING

The invention concerns a risk assessment device, in particular for the risk of a severe heart functional disorder such as sudden death due to heart disease, comprising an input unit which is adapted to record or read in an electrocardiogram as an input signal and output a corresponding output signal including a plurality of cardiac cycles and corresponding intervals, and a detection unit which is connected to the input unit and which is adapted to detect events of a predetermined nature in the output signal.

The intervals can be R—R intervals but also p—p intervals or other intervals of an electrocardiogram. Usually, an electrocardiogram includes a plurality of intervals of normal length. Particularly in the case of extrasystoles however intervals of reduced or increased length may occur, which do not correspond to a normal interval.

BACKGROUND OF THE ART

Published international application WO 99/23944 discloses a method and an apparatus which assess electrocardiograms, with the aim of obtaining parameters which can be associated with the individual risk of a person, by assessing electrocardiograms in the area of extrasystoles.

In the time domain, for example, an 'onset' is ascertained for that purpose. That is the difference in the mean values of the last normal RR-intervals before the extrasystole and the first normal RR-intervals after the extrasystole.

Another parameter in the time domain is the 'slope', That is the greatest retardation in frequency within a sequence of a plurality of heartbeat intervals after an extrasystole over a predetermined number of successive RR-intervals. The gradient of the regression degrees describing the retardation in frequency is ascertained. In conjunction with the slope its correlation coefficient is determined, that is to say a measurement in respect of the regularity of the slope which is formed by numerical averaging of a plurality of successive slope values.

It is known from WO 99/23944 that, with a low onset, a shallow slope or a low correlation coefficient of the slope, the risk of dying as matters progress is significantly increased.

SUMMARY OF THE INVENTION

The object of the present invention is to provide a device which is suitable for risk assessment and which can determine the risk of severe heart functional disorders with a degree of sensitivity which is high as possible and a level of specificity which is as high as possible. High sensitivity means that as many as possible of candidates for sudden death due to heart disease are warned and only a few candidates are overlooked, that is to say remain unwarned, in which respect admittedly there are also persons in respect of whom the risk as matters proceed is not confirmed are also warned. High specificity means that a warning does not happen in relation to most patients who are not endangered, but in actual fact there are also some patients who are not endangered, who are erroneously warned (that is to say disquieted).

In accordance with the invention that object is attained by a device of the kind set forth in the opening part of this specification, including a summing unit which is connected to the detection unit and the input unit and is adapted to add up the length of predetermined intervals connected to the detected event within the input signal and to output a corresponding sum parameter, and an evaluation unit which is adapted to evaluate the sum parameter under predetermined conditions and to output a risk parameter dependent on the evaluation. Evaluation of the sum parameter in the evaluation unit to form the risk parameter is typically effected in that the configuration in respect of time of the sum parameter is analysed and a risk parameter corresponding to the respective trend parameter in respect of time is formed.

In at least one embodiment, the detection unit detects ventricular extrasystoles as a predetermined event.

In many embodiments, the detection unit is connected to a selection unit that selects among the detected events those events which have a predetermined property.

In that respect the selection unit will typically select such ventricular extrasystoles which are involved, with a change in the morphology of a QRS-complex associated with the extrasystole, compared to QRS-complexes which are not linked to an extrasystole, in the output signal of the input unit.

Commonly, the selection unit will also select such ventricular extrasystoles in which a QRS-complex is at least 20% premature compared to the QRS-complexes of preceding intervals. The typical selection unit is one which selects such ventricular extrasystoles which are followed by an interval which is extended by at least 10% in relation to preceding intervals. For selection which goes still further, the selection unit is adapted to select a predetermined number of intervals which do not contain any extrasystole prior to and after a ventricular extrasystole, for forming the sum parameter. Those measures each in themselves and in particular in combination contribute to substantially avoiding misclassifications due to disturbances in the signal such as noise, hum or other signals which are superimposed on the electrocardiogram. The number of the intervals respectively considered, preceding or following an extrasystole, can be for example between 2 and 20 and can be used to predetermine the most appropriate values for sensitivity and specificity, in accordance with further conditions. In that respect the sequence of the stated features can be adapted to the given aspects of the signal in regard to signal quality and processing time and the arrangement of the measures can be interchanged.

In a further alternative configuration the detection unit includes an interval selection unit which is adapted to select for the formation of the sum parameter such intervals with which there are associated at least two ventricular extrasystoles which occur within a predetermined period of time. That period of time is commonly of the order of magnitude of an hour.

Supplementally or alternatively the object of the invention is attained in a risk assessment unit having an input unit which is adapted to record or read in an electrocardiographic input signal and to output a corresponding output signal including a plurality of cardiac cycles and corresponding intervals, and a first evaluation unit which is at least indirectly connected to the input unit and which is adapted to evaluate the output signal under predetermined conditions and to output a risk parameter dependent on the evaluation, characterised by a second evaluation unit which is connected to the first evaluation unit to take over the risk parameter as a first parameter and has at least one input for at least one further parameter and is adapted to calculate a risk signal corresponding to a probability of a severe heart functional disorder by linear combination of the parameters as it is usually determined by logistical regression, or by non-linear combination of the parameters.

It has been found that not only the risk parameter as described hereinbefore and formed from the sum parameter is a suitable input value for logistical regression analysis, but for example also the above-described onset or slope as well as the statistical fluctuation range of those values. However particularly specific and significant results are attained if the sum parameter or the configuration in respect of time thereof, besides age and blood pressure of a patient, are involved in the linear combination of the parameters.

In summary the essential aspects of the invention lie on the one hand in the formation of the described sum parameter and on the other hand in the linking of various risk parameters by a linear combination. Both aspects alone and independently of each other contribute to an improvement in sensitivity and specificity. The object of the invention is particularly well attained by a risk assessment device in which the sum parameter is one of the risk parameters which are involved in the parameter combination.

BRIEF DESCRIPTION OF THE DRAWINGS

The invention will now be described in greater detail by means of an embodiment with reference to the single Figure.

The Figure is a diagrammatic block circuit diagram of a risk assessment device according to the invention.

DETAILED DESCRIPTION OF THE PREFERRED EMBODIMENT

The risk assessment device 10 includes as its main component an ECG risk parameter branch 12 and a risk analyser 14 which in the illustrated embodiment are advantageously connected together but which can also be implemented separately from each other.

On the input side the ECG risk parameter branch 12 has a connection for an ECG measurement value pick-up 16. Alternatively, an ECG which is stored on a data carrier 18 can also be read in, by way of a second connection. On the output side the ECG risk parameter branch 12 is connected to an input of the risk analyser 14. In the illustrated embodiment the risk analyser 14 has two further parameter inputs 20 and 22.

On the output side the risk analyser 14 is connected to an output unit 24. The output unit can have an interface for further units which are connected downstream thereof, it can include a display in order to display a calculated value for example for the risk of a sudden death due to heart disease or however it may also include a threshold value unit which outputs an alarm signal whenever the calculated risk exceeds a limit value. Such a threshold value unit can moreover be connected to a therapy unit which is triggered when the threshold value is exceeded and which for example causes medicational therapy or electrotherapy for the heart.

In an alternative configuration the illustrated risk assessment device 10 is so designed that it is part of an implanted device which by means of the ECG input 16 and an input unit 26 connected thereto, is capable of recording as its input signal an ECG which is derived directly from the heart or obtained from another location in the interior of the body. A measurement value pick-up, for example a sense electrode of an electrode line, can be connected to the ECG unit 16, as is known to be used in relation to cardiac pacemakers. The input unit 26 includes the necessary input amplifiers and filters to process the input signal and to make a processed ECG signal available at its output.

The processed ECG signal is fed to a detection unit 28 which is adapted to detect the QRS-complexes contained in the input signal and in particular various kinds of extrasystoles in the processed ECG signal. Such extrasystoles are, inter alia, supraventricular extrasystoles, ventricular extrasystoles without a change in the morphology of the corresponding QRS-complex in the ECG (VES-1) and ventricular extrasystoles which are involved with a change in the morphology of the corresponding QRS-complex (VES-2). Hereinafter, in connection with extrasystoles, more detailed information will be set forth, in accordance with the classification system described herein, only when that is required to explain the function and the requirement involved.

From the detection unit 28 the processed ECG signal together with the information about detected extrasystoles passes to a selection unit 30 which, besides normal memory elements, includes a morphology comparison unit 32 which is adapted to detect variations in the morphology of a QRS-complex. For that purpose the morphology comparison unit 32 is connected to a signal portion memory 34 for storing the respective form or parameters extracted therefrom of that QRS-complex which was ascertained for the last-detected reference interval. In that respect, the reference interval is an interval which corresponds to a predetermined duration or a predetermined number of normal events and does not contain any extrasystole.

On the basis of the comparison of the signal portion stored in the signal portion memory 34 or the extracted parameters and the corresponding signal portion associated with a ventricular extrasystole or its extracted parameters, the morphology comparison unit 32 is capable of detecting variations in the morphology of a QRS-complex in connection with a ventricular extrasystole and outputting a corresponding marker signal for the ventricular extrasystole with a QRS-complex morphology variation (type VES-2) and the R—R interval preceding the ventricular extrasystole with the QRS morphology variation (type VES-2) and the following R-R interval. Following the morphology comparison unit 32 the processed ECG signal with the information about VES-2 extrasystoles which have occurred is fed to a reference interval comparison unit 36 of the selection unit 30. The reference interval comparison unit 30 serves for further selection of the intervals containing a ventricular extrasystole. For that purpose, the reference interval comparison unit 36 is connected to a reference interval memory 38 for storing a reference interval derived from the average of the last normal intervals. This usually involves a relatively small number of normal intervals, for example 5 intervals, in order to permit sufficiently rapid adaptation to physiological changes as constantly occur without any connection to extrasystoles. The reference interval comparison unit 36 is so adapted that it only selects such intervals containing a VES-2 extrasystole, in which the extrasystole is premature in relation to the reference interval at least by a predetermined limit value (typically 20%) and which have a post-extrasystole pause which is longer at least by a limit value (typically 10%) than the pause after the systole in the reference interval. In addition, the reference interval comparison unit 36 is adapted only to select such intervals containing VES-2 extrasystoles, which are preceded by a predetermined number of normal intervals and which are followed by an also predetermined number of normal intervals.

In that respect, depending on the given aspects of the signal, in terms of signal quality and processing time, the morphology comparison unit 32 in conjunction with the signal portion memory 34 can be interchanged with the reference interval comparison unit 36 in conjunction with the reference interval memory 38.

The information about the processed ECG signal and the selected intervals is available at the output of the reference interval comparison unit 36 or the morphology comparison unit 32, in the case of the above-described interchange of the functional units, and is applied to the input of an interval selection unit 40. The interval selection unit 40 executes a further selection in such a way that only those intervals are selected, which relate to at least two VES-2 extrasystoles which occur in succession within a predetermined time, in specific terms for example within an hour. If therefore only one VES-2 extrasystole occurs within that time, the corresponding interval is not selected. If more than one VES-2 extrasystole occurs within an hour, the corresponding intervals are selected. Once again, the processed ECG signal and the information about the selected intervals are available at the output of the interval selection unit 40 and thus at the input of the summing unit 42. The summing unit 42 is adapted to form the sum of the durations of the selected intervals. In addition the summing unit 42 is adapted to determine the sum of the selected intervals for a respective predetermined time, for example 24 hours, optionally in each case beginning at zero or floating over the predetermined period of time preceding the last VES-2 extrasystole. That therefore affords a kind of density function over the occurrence of intervals which are detected by the interval selection unit 40. That is applied to the input of a first evaluation unit 44. The first evaluation unit 44 is adapted to determine the trend pattern of the incoming sum parameters.

The sum parameter itself is already an indicator in respect of the risk of a sudden death due to heart disease. If the value of the sum parameter is high the risk of dying from sudden death due to heart disease is greater than when the value of the sum parameter is low. In addition a rising trend pattern, having regard to the scatter of the sum parameter, points to an increase in the risk of suffering sudden death due to heart disease.

The sum parameter at the output of the ECG risk parameter branch 12 or the trend pattern thereof can be added for example to a threshold value unit which, whenever the sum parameter or the trend pattern thereof exceeds a given limit value, gives an alarm which indicates a high risk of sudden death due to heart disease. It is also possible to connect to the threshold value unit a unit for delivering a medicament or for carrying out another preventive-therapeutic measure.

In the illustrated embodiment the sum parameter or the trend pattern thereof is applied to one of three inputs of the risk analyser 14. It is firstly fed to an interval scaling unit 50 of the risk analyser 14, in which the continuous sum parameter or the trend pattern thereof is subjected to an interval scaling procedure. The value describing the respective interval in which a current sum parameter or the trend pattern thereof falls is multiplied in a multiplication unit 52 by a previously determined coefficient. In the illustrated embodiment this is the coefficient $b_1$. For that purpose the multiplication unit 52 is connected to the interval scaling unit 50.

The signals at the parameter inputs 20 and 22 are also subjected to interval scaling in accordance with their respective magnitude in corresponding interval scaling units 54 and 56 and the scale value describing the respective interval is multiplied in multiplication units 58 and 60 by the previously determined coefficients $b_2$ and $b_3$. Therefore, three different scale values multiplied by the respective coefficients are available at the outputs of the multiplication units 52, 58 and 60. Those three values, together with a constant 61, are added together in a summing unit 62. A parameter sum is available at the output of the summing unit 62, which parameter sum in a subsequent exponential unit 64 is accounted for in such a way that a value which corresponds to the Euler's number $e^{parameter\ sum}$ occurs at the output of the exponential unit 64. That value is divided in the subsequent computing unit 66 by the sum of that value plus 1. A risk factor is available at the output of the computing unit 66, which describes the probability of dying from a sudden death due to heart disease and the determination of which involves not just the sum parameter from the ECG risk parameter branch 12 but by way of the parameter inputs 20 and 22 also such risk factors as age or blood pressure. Those risk parameters are balanced with each other in the risk analyser 14 on the basis of the approach of logistical regression. In this respect the described structure of the risk analyser 14 leads to a calculation, in which the output value p thereof depends on the input values X1, X2 and X3, as follows:

$$p = \frac{e^{(b_1 \cdot X1 + b_2 \cdot X2 + b_3 \cdot X3 + a)}}{1 + e^{(b_1 \cdot X1 + b_2 \cdot X2 + b_3 \cdot X3 + a)}}$$

In that respect the coefficients $b_1$, $b_2$ and $b_3$ and a are matched in the manner which is usual for logistical regression procedures.

It has been found that a corresponding risk assessment device can determine the risk of sudden death due to heart disease both with a high level of sensitivity and also with a high degree of specificity. The aim of values which are as high as possible both in respect of sensitivity and also in respect of specificity is achieved in the device according to the invention by one of the following measures alone or a suitable combination thereof:

- selection of VES-2 extrasystoles in accordance with predetermined criteria and limit values;
- formation of sum parameters and trend parameters derived therefrom;
- consideration of risk parameters which have been validated on the basis of a logistical regression model; and
- formation of risk factors which are calculated on the basis of weighting coefficients which are established in accordance with the aim involved, and interval-scaled risk parameters.

What is claimed is:

1. A risk assessment device, for assessing the risk of a severe heart functional disorder, comprising:
   an input unit to record, or read in, an electrocardiographic input signal and to output a corresponding processed output signal;
   a detection unit, connected to the input unit, to detect events of a predetermined nature in the output signal;
   a summing unit connected to the detection unit and the input unit, the summing unit adding up a length of predetermined intervals connected to a detected event within the input signal and outputting a corresponding sum parameter; and
   an evaluation unit to evaluate the sum parameter under predetermined conditions and to output a risk parameter which is dependent on the evaluation.

2. The risk assessment device of claim 1 wherein the predetermined events are from a group consisting of a QRS-complex, an extrasystole, and a combination thereof.

3. The risk assessment device of claim 2, further comprising a selection unit, connected to the detection unit, to select among the detected events such events which have one or more predetermined properties.

4. The risk assessment device of claim 3, wherein the selection unit selects ventricular extrasystoles which involve a change in a morphology of a QRS-complex associated with an extrasystole in relation to QRS-complexes not linked to an extrasystole, in the output signal of the input unit.

5. The risk assessment device of claim 4, wherein the selection unit selects ventricular VES-2 extrasystoles that are followed by an interval which is increased in length by a predetermined limit value in comparison with preceding intervals not containing any extrasystoles.

6. The risk assessment device claim 5, wherein the selection unit selects, to form a reference interval, a predetermined number of intervals not containing any extrasystoles prior to and after a VES-2 extrasystole.

7. The risk assessment device of claim 6, further comprising an interval selection unit, connected to the selection unit, to select intervals that are associated with at least two VES-2 extrasystoles which occur within a predetermined period of time, to form the sum parameter.

8. The risk assessment device of claim 7, wherein the predetermined period of time is of the order of magnitude of one hour.

9. The risk assessment device of claim 8, wherein the evaluation unit forms a trend pattern by evaluating the sum parameter, in such a way that the risk parameter corresponds to a trend of the sum parameter.

10. The risk assessment device of claim 9, further comprising a second evaluation unit, connected to the evaluation unit, to take over the risk parameter as a first parameter, the second evaluation unit having at least one input for at least one further parameter, the second evaluation unit calculating a risk signal corresponding to a probability of a severe heart functional disorder based on a linear combination of at least two of the parameters, as is commonly determined by logistical regression, or by non-linear combination of at least two of the parameters.

11. The risk assessment device of claim 3, wherein the selection unit selects ventricular VES-2 extrasystoles in which a QRS-complex is premature at least by a predetermined limit value, when compared to QRS-complexes of preceding intervals containing no extrasystoles.

12. The risk assessment device of claim 11, wherein the selection unit selects ventricular VES-2 extrasystoles that are followed by an interval which is increased in length by a predetermined limit value in comparison with preceding intervals not containing any extrasystoles.

13. The risk assessment device of claim 12, wherein the selection unit selects, to form a reference interval, a predetermined number of intervals not containing any extrasystoles prior to and after a VES-2 extrasystole.

14. The risk assessment device of claim 13, further comprising an interval selection unit, connected to the selection unit, to select intervals that are associated with at least two VES-2 extrasystoles which occur within a predetermined period of time, to form the sum parameter.

15. The risk assessment device of claim 14, wherein the predetermined period of time is of the order of magnitude of one hour.

16. The risk assessment device of claim 15, wherein the evaluation unit forms a trend pattern by evaluating the sum parameter, in such a way that the risk parameter corresponds to a trend of the sum parameter.

17. The risk assessment device of claim 16, further comprising a second evaluation unit, connected to the evaluation unit, to take over the risk parameter as a first parameter, the second evaluation unit having at least one input for at least one further parameter, the second evaluation unit calculating a risk signal corresponding to a probability of a severe heart functional disorder based on a linear combination of at least two of the parameters, as is commonly determined by logistical regression, or by non-linear combination of at least two of the parameters.

18. The risk assessment device of claim 1, further comprising a selection unit, connected to the detection unit, to select among the detected events such events which have one or more predetermined properties.

19. The risk assessment device of claim 18, wherein the selection unit selects ventricular extrasystoles which involve a change in a morphology of a QRS-complex associated with an extrasystole in relation to QRS-complexes not linked to an extrasystole, in the output signal of the input unit.

20. The risk assessment device of claim 19, wherein the selection unit selects ventricular VES-2 extrasystoles that are followed by an interval which is increased in length by a predetermined limit value in comparison with preceding intervals not containing any extrasystoles.

21. The risk assessment device of claim 20, wherein the selection unit selects, to form a reference interval, a predetermined number of intervals not containing any extrasystoles prior to and after a VES-2 extrasystole.

22. The risk assessment device of claim 21, further comprising an interval selection unit, connected to the selection unit, to select intervals that are associated with at least two VES-2 extrasystoles which occur within a predetermined period of time, to form the sum parameter.

23. The risk assessment device of claim 22, wherein the predetermined period of time is of the order of magnitude of one hour.

24. The risk assessment device of claim 23, wherein the evaluation unit forms a trend pattern by evaluating the sum parameter, in such a way that the risk parameter corresponds to a trend of the sum parameter.

25. The risk assessment device of claim 24, further comprising a second evaluation unit, connected to the evaluation unit, to take over the risk parameter as a first parameter, the second evaluation unit having at least one input for at least one further parameter, the second evaluation unit calculating a risk signal corresponding to a probability of a severe heart functional disorder based on a linear combination of at least two of the parameters, as is commonly determined by logistical regression, or by non-linear combination of at least two of the parameters.

26. The risk assessment device of claim 18, wherein the selection unit selects ventricular VES-2 extrasystoles in which a QRS-complex is premature at least by a predetermined limit value, when compared to QRS-complexes of preceding intervals containing no extrasystoles.

27. The risk assessment device of claim 26, wherein the selection unit selects ventricular VES-2 extrasystoles that are followed by an interval which is increased in length by a predetermined limit value in comparison with preceding intervals not containing any extrasystoles.

28. The risk assessment device of claim 27, wherein the selection unit selects, to form a reference interval, a predetermined number of intervals not containing any extrasystoles prior to and after a VES-2 extrasystole.

29. The risk assessment device of claim 28, further comprising an interval selection unit, connected to the selection unit, to select intervals that are associated with at least two VES-2 extrasystoles which occur within a predetermined period of time, to form the sum parameter.

30. The risk assessment device of claim 29, wherein the predetermined period of time is of the order of magnitude of one hour.

31. The risk assessment device of claim 30, wherein the evaluation unit forms a trend pattern by evaluating the sum parameter, in such a way that the risk parameter corresponds to a trend of the sum parameter.

32. The risk assessment device of claim 31, further comprising a second evaluation unit, connected to the evaluation unit, to take over the risk parameter as a first parameter, the second evaluation unit having at least one input for at least one further parameter, the second evaluation unit calculating a risk signal corresponding to a probability of a severe heart functional disorder based on a linear combination of at least two of the parameters, as is commonly determined by logistical regression, or by non-linear combination of at least two of the parameters.

33. The risk assessment device of claim 1, wherein the evaluation unit forms a trend pattern by evaluating the sum parameter, in such a way that the risk parameter corresponds to a trend of the sum parameter.

34. The risk assessment device of claim 33, further comprising a second evaluation unit, connected to the evaluation unit, to take over the risk parameter as a first parameter, the second evaluation unit having at least one input for at least one further parameter, the second evaluation unit calculating a risk signal corresponding to a probability of a severe heart functional disorder based on a linear combination of at least two of the parameters, as is commonly determined by logistical regression, or by non-linear combination of at least two of the parameters.

35. The risk assessment device of claim 1, further comprising a second evaluation unit, connected to the evaluation unit, to take over the risk parameter as a first parameter, the second evaluation unit having at least one input for at least one further parameter, the second evaluation unit calculating a risk signal corresponding to a probability of a severe heart functional disorder based on a linear combination of at least two of the parameters, as is commonly determined by logistical regression, or by non-linear combination of at least two of the parameters.

36. A risk assessment device, for assessing the risk of a severe heart functional disorder, comprising an input unit to record, or read in, an electrocardiographic input signal and to output a corresponding processed output signal;

a detection unit, connected to the input unit, to detect events of a predetermined nature in the output signal, the predetermined events being from a group consisting of a QRS-complex, an extrasystole, and a combination thereof;

a selection unit, connected to the detection unit, to select among the detected events such events which have one or more predetermined properties, wherein the selection unit selects ventricular extrasystoles which involve a change in a morphology of a QRS-complex associated with an extrasystole in relation to QRS-complexes not linked to an extrasystole, in the output signal of the input unit, and wherein the selection unit further selects ventricular VES-2 extrasystoles in which the QRS-complex is premature at least by a predetermined limit value, when compared to the QRS-complexes of preceding intervals containing no extrasystoles, and wherein the selection unit further selects ventricular VES-2 extrasystoles that are followed by an interval which is increased in length by a predetermined limit value in comparison with preceding intervals not containing any extrasystoles, and wherein the selection unit further selects, for formation of a reference interval, a predetermined number of intervals not containing any extrasystoles prior to and after a VES-2 extrasystole;

a summing unit connected to the detection unit and the input unit, the summing unit adding up a length of predetermined intervals connected to a detected event within the input signal and outputting a corresponding sum parameter;

an evaluation unit to evaluate the sum parameter under predetermined conditions and to output a risk parameter which is dependent on the evaluation, the evaluation unit forming a trend pattern by evaluating the sum parameter, in such a way that the risk parameter corresponds to a trend of the sum parameter;

an interval selection unit, connected to the selection unit, to select intervals that are associated with at least two VES-2 extrasystoles which occur within a predetermined period of time, to form the sum parameter, wherein the predetermined period of time is of the order of magnitude of one hour; and a second evaluation unit, connected to the evaluation unit, to take over the risk parameter as a first parameter and to calculate a risk signal, the second evaluation unit having at least one input for at least one further parameter, the second evaluation unit calculating the risk signal corresponding to a probability of a severe heart functional disorder based on a linear combination of the parameters, as is commonly determined by logistical regression, or by non-linear combination of the parameters.

* * * * *